(12) United States Patent
Shoshtaev

(10) Patent No.: US 10,736,682 B2
(45) Date of Patent: Aug. 11, 2020

(54) LAMINAR FIXATION DEVICE AND METHOD

(71) Applicant: Life Spine, Inc., Huntley, IL (US)

(72) Inventor: Eugene Shoshtaev, Del Mar, CA (US)

(73) Assignee: LIFE SPINE, INC., Huntley, IL (US)

( * ) Notice: Subject to any disclaimer, the term of this patent is extended or adjusted under 35 U.S.C. 154(b) by 0 days.

(21) Appl. No.: 15/949,661

(22) Filed: Apr. 10, 2018

(65) Prior Publication Data

US 2018/0289404 A1    Oct. 11, 2018

Related U.S. Application Data

(60) Provisional application No. 62/483,676, filed on Apr. 10, 2017.

(51) Int. Cl.
*A61B 17/70* (2006.01)
*A61B 17/84* (2006.01)
(Continued)

(52) U.S. Cl.
CPC ........ *A61B 17/842* (2013.01); *A61B 17/7053* (2013.01); *A61B 17/7083* (2013.01);
(Continued)

(58) Field of Classification Search
CPC ....... A61B 17/70–7046; A61B 17/7049–7053; A61B 17/7074–7092; A61B 17/842
See application file for complete search history.

(56) References Cited

U.S. PATENT DOCUMENTS 5,961,517 A * 10/1999 Biedermann ...... A61B 17/7002
606/104
8,066,739 B2 * 11/2011 Jackson ............. A61B 17/7008
606/246
(Continued)

FOREIGN PATENT DOCUMENTS

EP    2777569 A1    9/2014

OTHER PUBLICATIONS

International Preliminary Report on Patentability for PCT PCT/US2018/026883 dated Oct. 24, 2019, 8 pages.
(Continued)

*Primary Examiner* — Nicholas J Plionis
*Assistant Examiner* — Steven J Cotroneo
(74) *Attorney, Agent, or Firm* — Foley & Lardner LLP

(57) ABSTRACT

A laminar fixation system includes an implant and a implant installation tool for use with laminar fixation tape for retaining a spine rod relative to a vertebra of the spine. The implant has a spine rod locking portion, a laminar fixation tape channel, and a laminar fixation tape locking portion. The implant installation tool has a laminar fixation tape locking actuator for manipulating the laminar tape locking portion of the implant, and a laminar fixation tape tensioning sub-assembly for tensioning laminar fixation tape received in the implant. The laminar fixation tape locking actuator and the laminar fixation tape tensioning sub-assembly of the installation tool each operates independent of each other. Attachment of the implant to a spine rod via the spine rod locking portion of the implant is independent of laminar fixation tape tensioning and laminar tape fixation to the implant.

16 Claims, 8 Drawing Sheets

(51) Int. Cl.
*A61B 17/88* (2006.01)
*A61B 17/00* (2006.01)

(52) U.S. Cl.
CPC ............... *A61B 17/8869* (2013.01); *A61B 2017/00367* (2013.01); *A61B 2017/00477* (2013.01)

(56) References Cited

U.S. PATENT DOCUMENTS

| | | | | |
|---|---|---|---|---|
| 8,728,083 | B2* | 5/2014 | Baccelli | A61B 17/7053 606/86 A |
| 9,173,685 | B2* | 11/2015 | Lindquist | A61B 17/7049 |
| 9,757,167 | B2* | 9/2017 | Hsu | A61B 17/7076 |
| 10,022,159 | B2* | 7/2018 | Simpson | A61B 17/8869 |
| 10,307,186 | B2* | 6/2019 | Schafer | A61B 17/7053 |
| 2005/0192570 | A1* | 9/2005 | Jackson | A61B 17/7085 606/914 |
| 2005/0228375 | A1 | 10/2005 | Mazda et al. | |
| 2006/0069391 | A1* | 3/2006 | Jackson | A61B 17/7038 606/62 |
| 2009/0138048 | A1* | 5/2009 | Baccelli | A61B 17/8869 606/263 |
| 2011/0106185 | A1* | 5/2011 | Gil | A61B 17/7022 606/86 R |
| 2011/0112581 | A1* | 5/2011 | Clement | A61B 17/7053 606/264 |
| 2014/0094850 | A1* | 4/2014 | Clement | A61B 17/7001 606/263 |
| 2014/0257397 | A1* | 9/2014 | Akbarnia | A61B 17/8869 606/263 |
| 2016/0262806 | A1* | 9/2016 | Hsu | A61B 17/7076 |
| 2019/0183553 | A1* | 6/2019 | Bosshard | A61B 17/8861 |

OTHER PUBLICATIONS

International Search Report for International Application No. PCT/US2018/026883, dated Jul. 24, 2018, 12 pages.

* cited by examiner

LAMINAR FIXATION DEVICE AND METHOD

CROSS-REFERENCE TO RELATED APPLICATIONS

This U.S. non-provisional patent application claims the benefit of and/or priority under 35 U.S.C. § 119(e) to U.S. provisional patent application Ser. No. 62/483,676 filed Apr. 10, 2017 titled "Laminar Fixation Device and Method," the entire contents of which is specifically incorporated herein by reference.

FIELD OF THE INVENTION

The present invention relates to systems, implants and methods for orthopedic fixation of the spine and, more particularly, to systems, implants and methods for retaining a spine rod relative to a vertebra of the spine.

BACKGROUND OF THE INVENTION

Spine issues such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spine disorders typically result in symptoms including deformity, pain, nerve damage, and partial or complete loss of mobility. Non-surgical treatments, such as medication, rehabilitation and exercise can be effective, however, may fail to relieve the symptoms associated with these disorders. In some cases, non-surgical treatment is not an option. If non-surgical treatment fails or is not available, surgical treatment is required.

Surgical treatment of the aforementioned spine disorders includes correction, fusion, fixation, discectomy, laminectomy, and implants. Correction treatments used for positioning, alignment and stabilization of the spine employ implants such as spine (vertebral) rods and vertebral bone screw assemblies that provide connection to the spine rod, as well as other implants. Because of complex anatomies, severe spinal deformities, compromised pedicle anatomy, and/or poor vertebral bone quality, vertebral bone screw assemblies cannot be used. In these cases a laminar band and associated implant (a laminar fixation implant) is used to connect the spine rod to a vertebra, wherein the implant attaches to the spine rod and the band is received around the lamina or sub-lamina of the vertebra utilizing the strength of the laminar cortical bone. Most laminar fixation implants are installed using an installation tool specifically designed for the particular laminar fixation implant, creating a laminar fixation system.

While there are many styles of laminar fixation implants and laminar fixation systems, most are generally awkward, cumbersome and/or difficult to effectively use. There is therefore a need for a more efficient laminar fixation implant and/or laminar fixation system.

SUMMARY OF THE INVENTION

A laminar fixation system includes a laminar fixation implant and a laminar fixation implant installation tool for use with laminar fixation tape for retaining a spine rod relative to a vertebra of the spine.

The laminar fixation implant has a spine rod locking portion, a laminar fixation tape channel, and a laminar fixation tape locking portion. The laminar fixation implant installation tool has a laminar fixation implant retention mechanism, a laminar fixation tape locking actuator, and a laminar fixation tape tensioning sub-assembly. The separate laminar fixation tape tensioning sub-assembly and the laminar fixation tape locking portion allows independent manipulation of the tensioning of the laminar fixation tape and the locking thereof to the laminar fixation implant. The separate spine rod locking portion also allows locking of the laminar fixation implant to a spine rod independent of the tensioning and locking of the laminar fixation implant to a spine rod.

The spine rod locking portion of the laminar fixation implant includes a spine rod engagement segment configured to fit about a spine rod, a threaded bore extending from a top of the spine rod engagement segment to a spine rod reception area of the rod engagement segment, and a set screw disposed in the threaded bore to fix the rod engagement segment to the spine rod.

The laminar fixation tape locking portion of the laminar fixation implant includes a threaded bore extending from a top of the laminar fixation implant to the laminar fixation tape channel of the laminar fixation, a ball disposed in the threaded bore proximate the laminar fixation tape channel, and a set screw for pressing the ball against the laminar fixation tape, the ball inhibiting fraying of a portion of the tensioned laminar fixation tape within the laminar fixation tape channel.

Further aspects of the present invention will become apparent from consideration of the figures and the following description of the invention. A person skilled in the art will realize that other forms of the invention are possible and that the details of the invention can be modified in a number of respects without departing from the inventive concept. The following figures and description are to be regarded as illustrative in nature and not restrictive.

BRIEF DESCRIPTION OF THE DRAWINGS

The features of the invention will be better understood by reference to the accompanying drawings which illustrate a form of the present invention, wherein.

Figure 1:
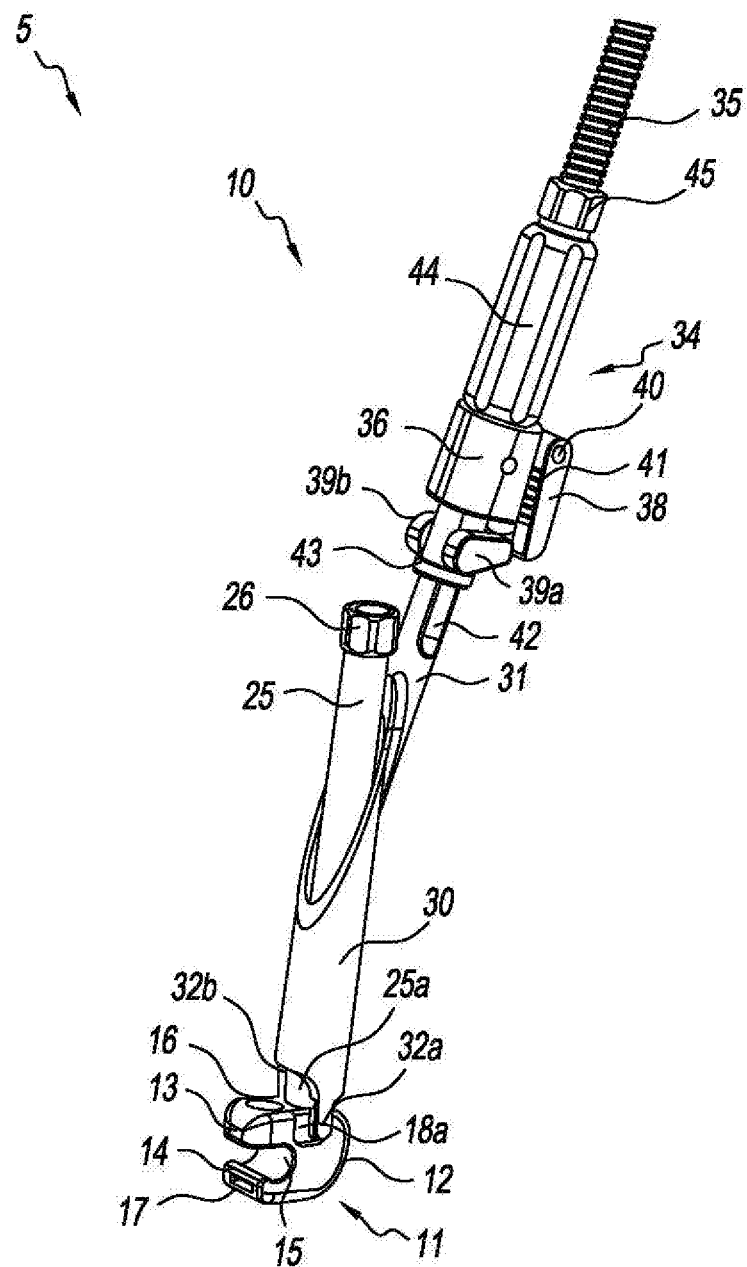
FIG. 1 is an isometric view of the present laminar fixation system fashioned in accordance with the present principles.
Figure 2:
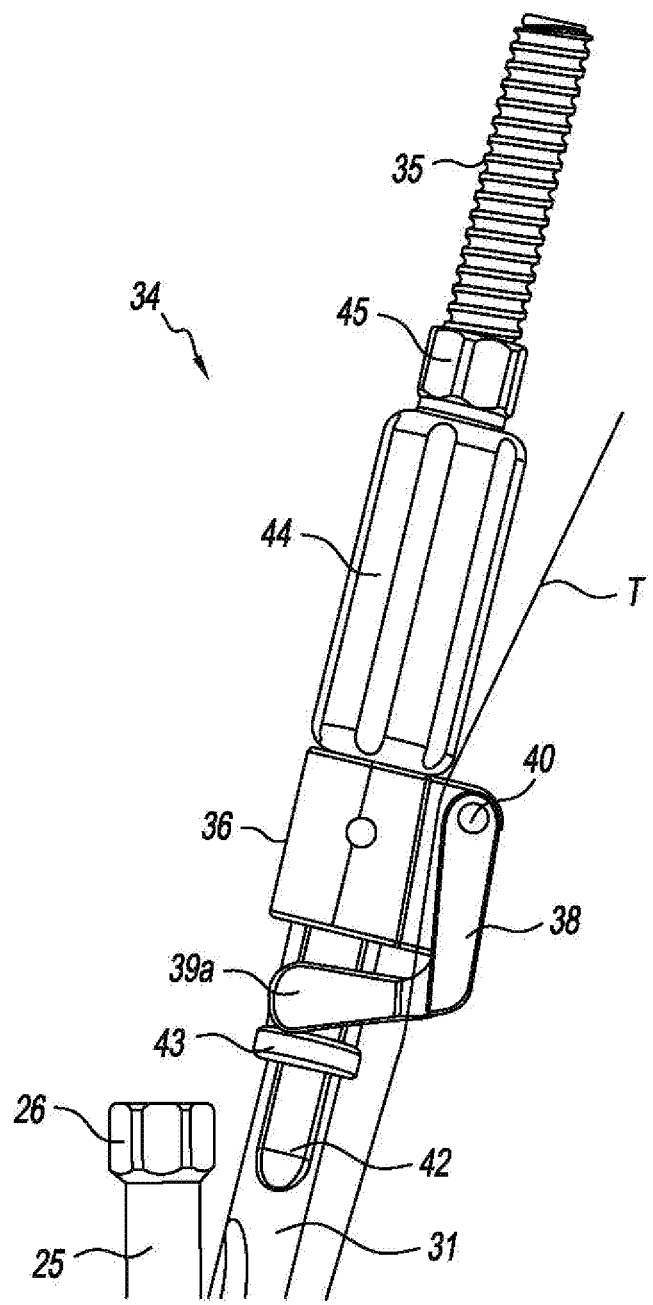
FIG. 2 is an enlarged isometric view of a laminar fixation tape tensioning sub-assembly of the laminar fixation implant installation tool of the present laminar fixation system of FIG. 1 shown with laminar fixation tape therein, the laminar fixation tape tensioning sub-assembly in a tape unlocked state.
Figure 3:
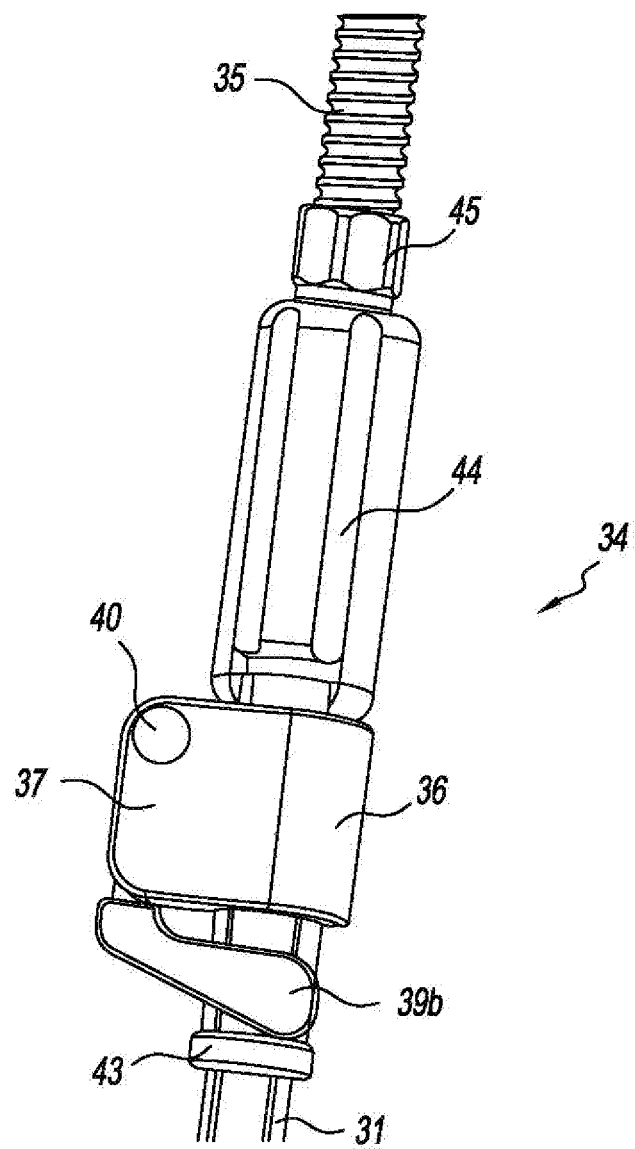
FIG. 3 is an enlarged opposite side view to FIG. 2 of the laminar fixation tape tensioning sub-assembly of the laminar fixation implant installation tool of the present laminar fixation system of FIG. 1 shown without laminar fixation tape therein.
Figure 4:
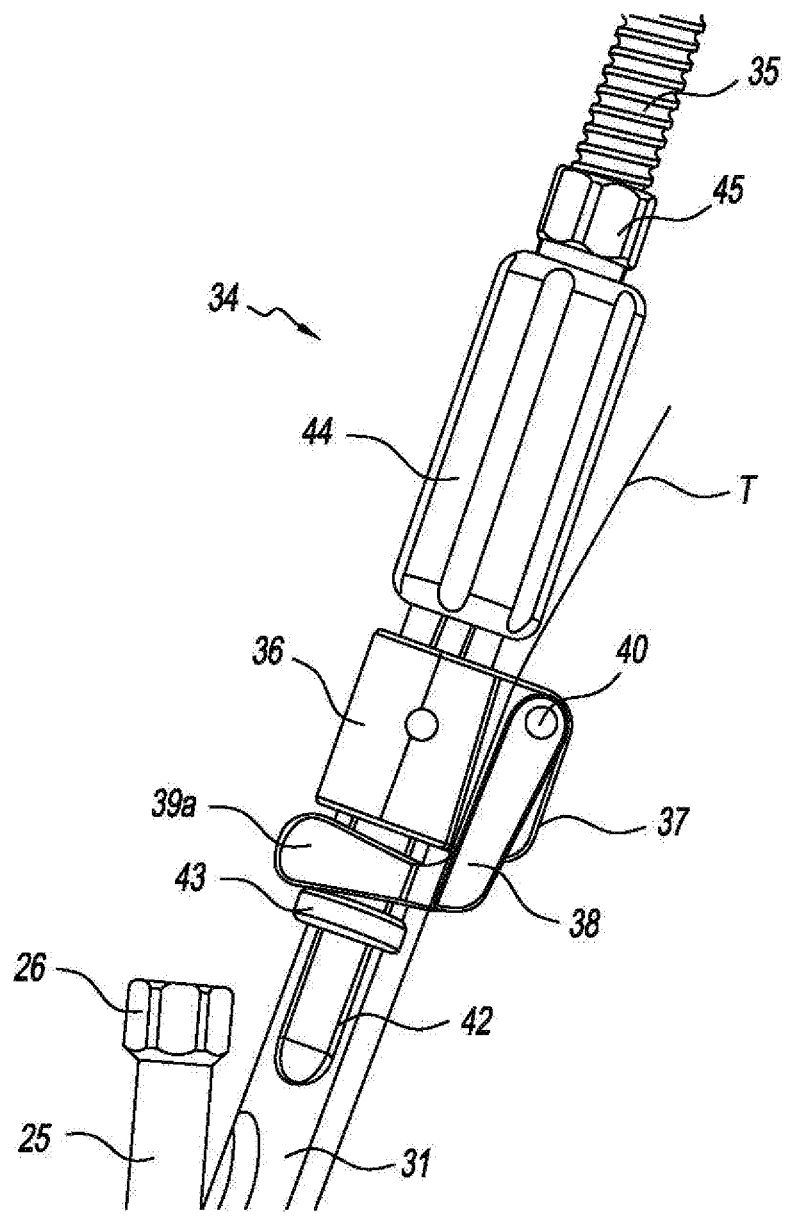
FIG. 4 is an enlarged isometric view of the laminar fixation tape tensioning sub-assembly shown with laminar fixation tape therein and in a tape locked state which allows tensioning of the laminar fixation tape from actuation of a tensioning hex drive of the laminar fixation tape tensioning sub-assembly.
Figure 5:
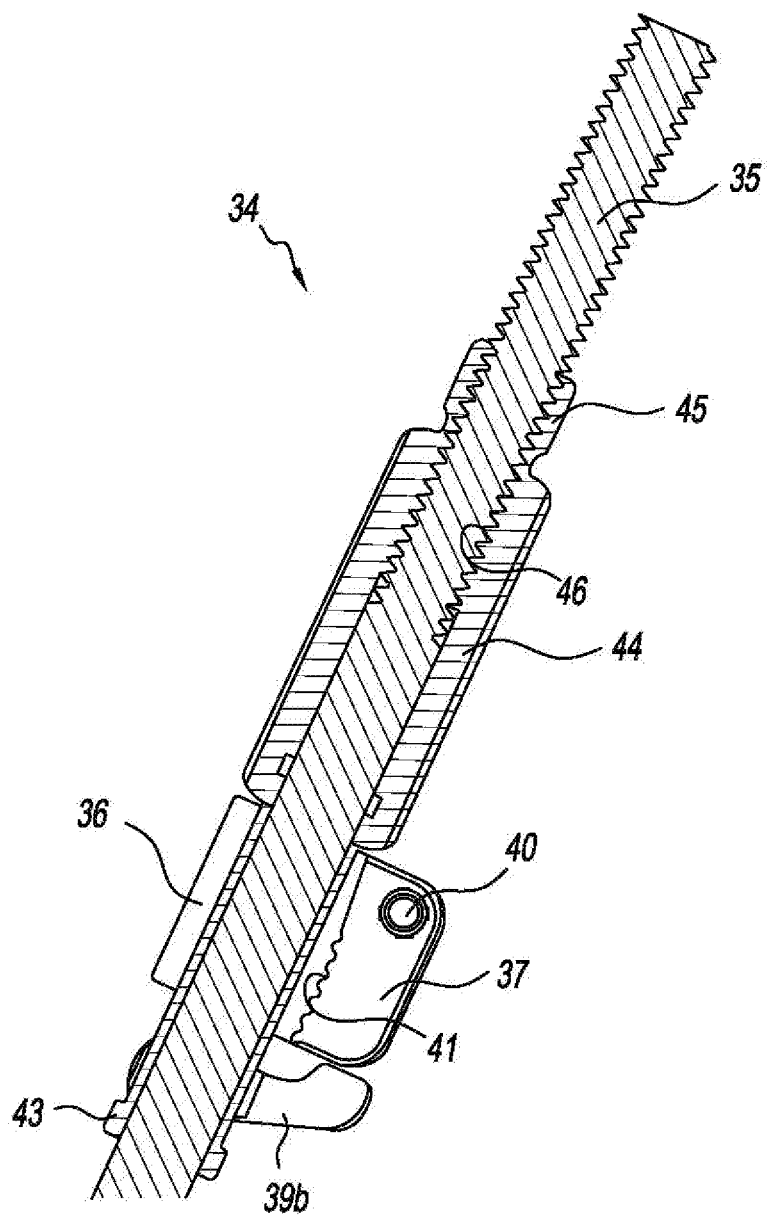
FIG. 5 is a sectional view of the laminar fixation tape tensioning sub-assembly shown without laminar fixation tape.
Figure 6:
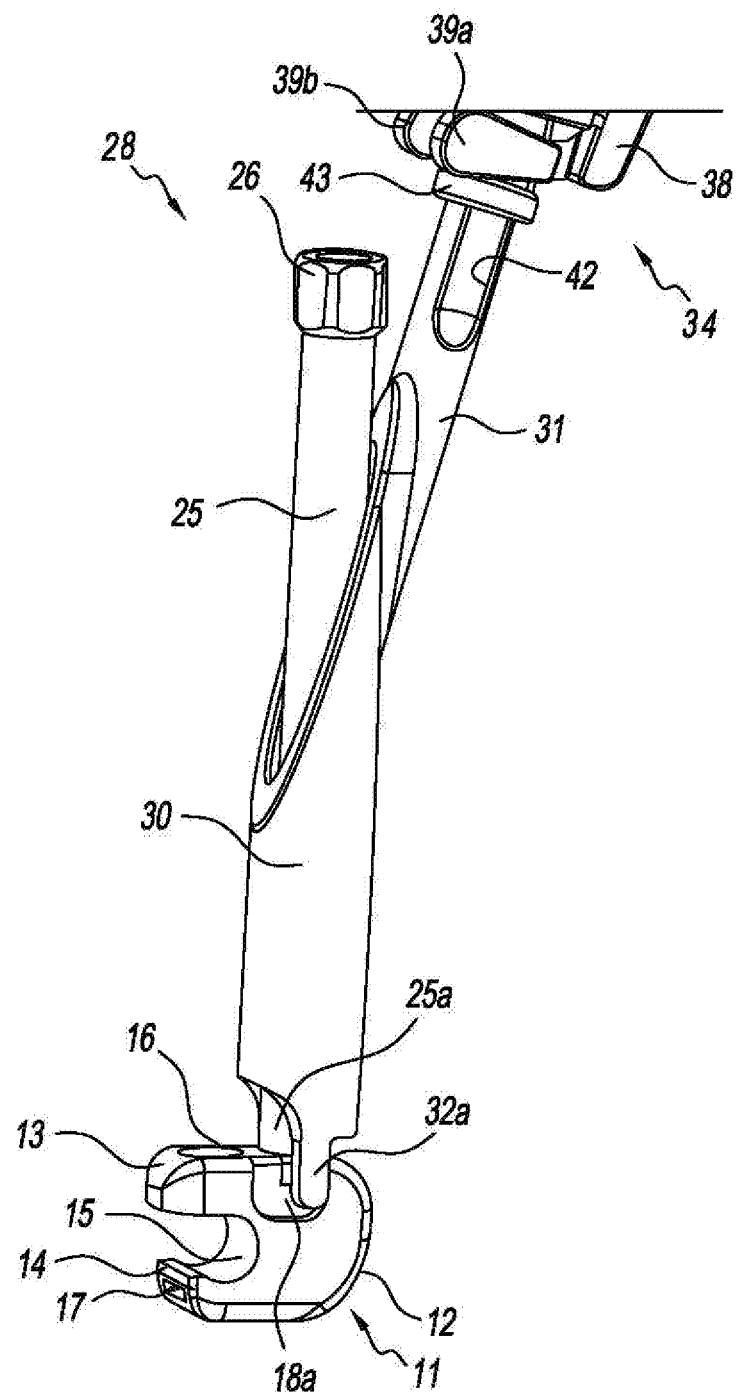
FIG. 6 is an isometric view of the laminar fixation tape locking actuator of the laminar fixation implant installation tool shown connected to the laminar fixation implant.

It should be appreciated that dimensions of the components, structures, and features of the present laminar fixation system can be altered as desired.

DETAILED DESCRIPTION OF THE INVENTION

Referring to FIGS. 1-8, there is shown a laminar fixation system generally designated 5, fashioned in accordance with the present principles. The laminar fixation system 5 includes a laminar fixation implant 11, and a laminar fixation implant installation instrument or tool 10. The laminar fixation system uses laminar fixation tape T (or laminar fixation band) for retaining a spine rod (not shown) relative to a vertebra of the spine (not shown). Particularly, the laminar fixation implant 11 is configured to attach onto a spine rod and be held to the lamina, sub-lamina, or other part of a vertebra (not shown) via laminar fixation tape T (or a laminar fixation band) via a laminar tape loop 1 (see FIG. 7) that wraps around the lamina, sub-lamina, or other part of a vertebra.

The laminar fixation implant 11 is characterized by a body 12 formed of a biocompatible material such as, but not limited to, titanium, stainless steel, an alloy thereof, ceramic, PEEK, other plastics or polymers, or other bio-compatible material having appropriate characteristics for its intended purpose as described herein. The body 12 defines a top, a bottom, a first lateral side, a second lateral side, a front end, and a rear end, the nomenclature first and second, and front and rear being arbitrary. A rod retention area 15 is provided at the front end of the laminar fixation implant 11 which defines an upper extension 13 and a lower extension 14. The upper extension 13 has a threaded bore 16 that extends from the top of the upper extension 13 to the bottom of the upper extension 13. A set screw 20 is disposed in the threaded bore 16. The threaded bore 16 and set screw 20 provides a locking mechanism for fixing the implant 11 onto a spine rod (not shown). The first lateral side has a first cutout 18a proximate the top of the implant body 12, while the second lateral side has a second cutout 18b proximate the top of the body of the implant body. The first and second cutouts 18a, 18b are preferably, but not necessarily, J-shaped. The first and second cutouts 18a, 18b are configured to releasably receive retention features (i.e. tangs 32a, 32b) of the installation tool 10.

The laminar fixation implant 11 further includes a passage 17 that extends from the lower extension 14 to the rear of the body 12 that is sized to receive laminar fixation tape (or band) T. The passage 17 allows the laminar fixation tape to freely pass therethrough in order to form a loop 1 (see FIG. 7) around the laminar or other bony portion of a vertebra (not shown). A locking mechanism is provided in the implant for locking/fixing the laminar fixation tape relative to the implant. A threaded bore 21 is provided in the implant body 12 that extends from the top of the body to the laminar fixation tape passage 17. A movable ball 23 is provided in the threaded bore 21 as well as a set screw 24. Threading of the set screw 24 onto the ball 23, moves the ball 23 toward and against the laminar fixation tape (see FIG. 7). Because of its shape, the ball 23 fixes the laminar fixation tape without or with minimal fraying of the laminar fixation tape.

Figure 7:
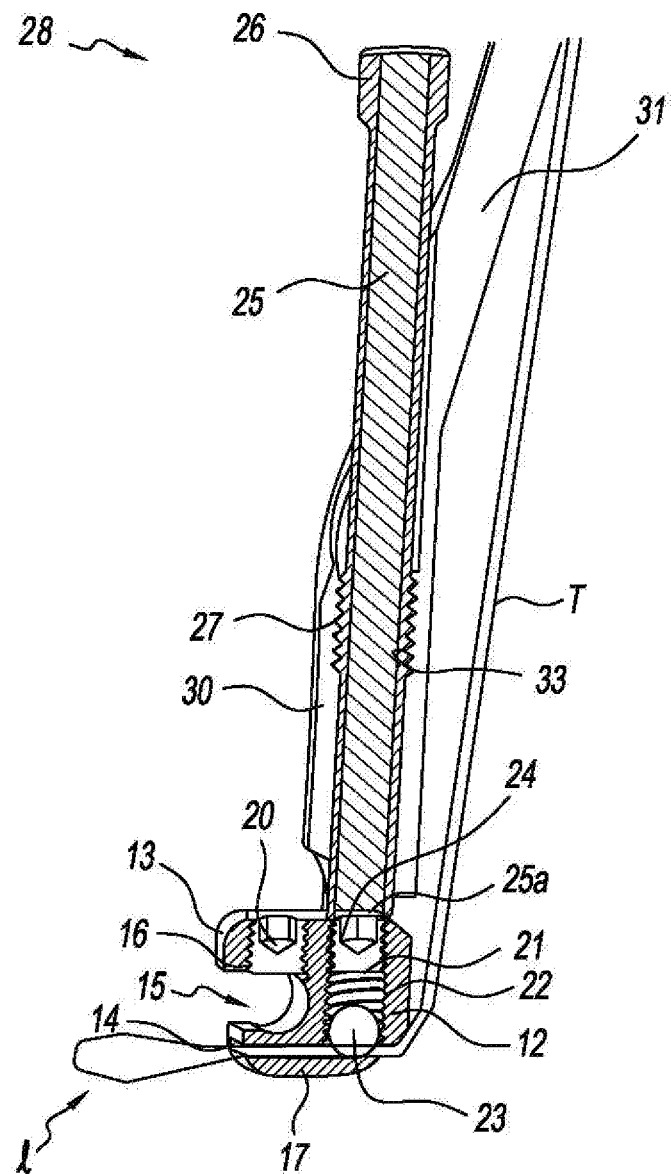
FIG. 7 is a sectional view of the laminar fixation tape locking actuator of the laminar fixation implant installation tool holding the laminar fixation implant and shown with laminar fixation tape illustrating that a rod set screw thereof locks the laminar fixation implant onto a spine rod, and a laminar tape set screw and ball locks a laminar tape loop in place after tensioning of the laminar fixation tape is complete.
Figure 8:
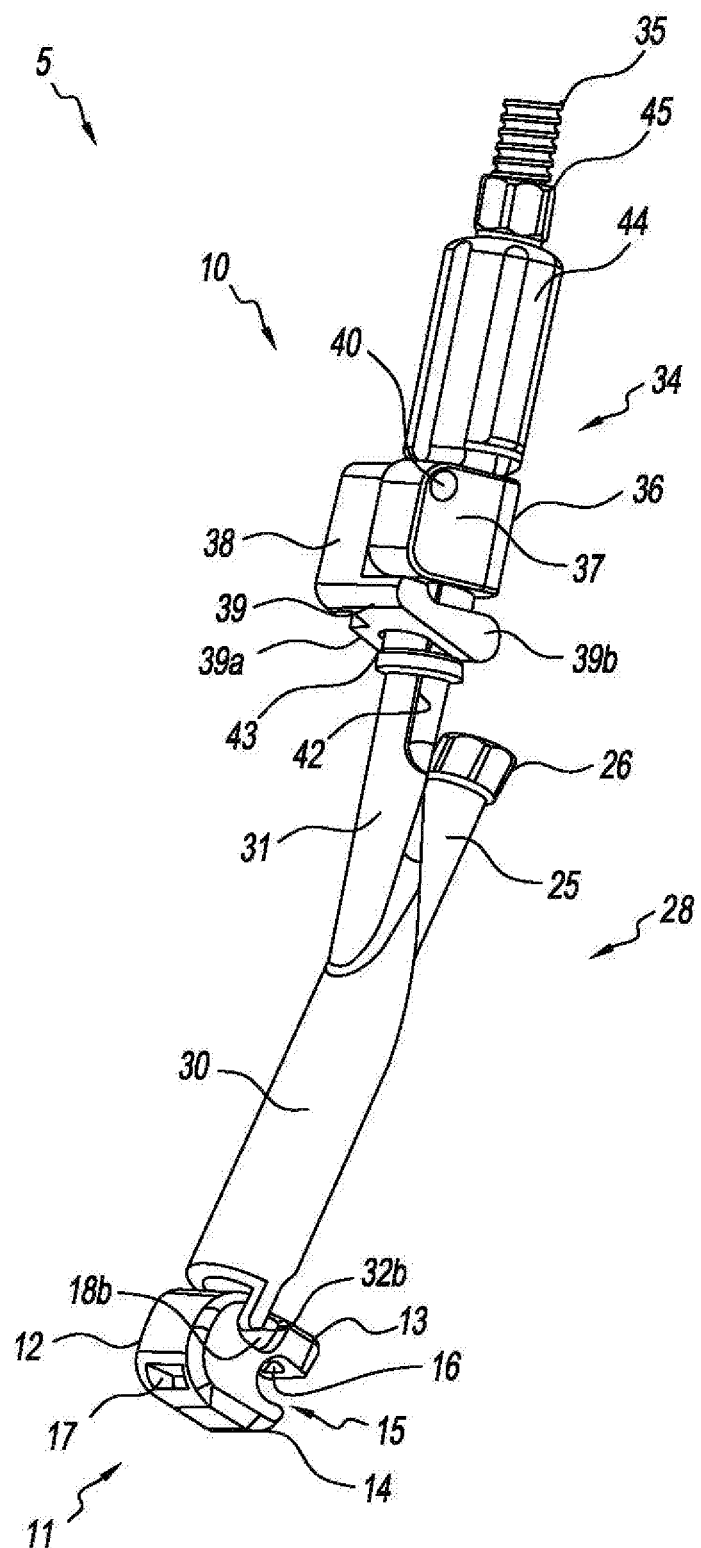
FIG. 8 is an isometric view of the laminar fixation system of FIG. 1 showing an opposite side view thereof.

The laminar installation tool 10 includes an implant retention portion consisting of the first and second tangs 32a, 32b that engage the first and second cutouts 18a, 18b. The first and second tangs 32a, 32b are disposed at the end of a tubular body 30 of the installation tool 10 which is also a part of the actuation mechanism for fixing the laminar fixation tape in and relative to the implant. As seen in FIG. 7, internal threads 33 are disposed in the tubular body 30 that engage external threads 27 of an actuation member 25. One end of the actuation member 25 has a driver 25a that is configured to engage the set screw 24, while the other end of the actuation member 25 has a head 26 configured to allow a tool (not shown) to engage and rotate the actuation member 25. Rotation of the actuation member 25 in a first direction advances the set screw 24 downward to engage the ball 23 which engages and fixes the laminar fixation tape.

The laminar fixation tool 10 also includes a tensioning sub-assembly or mechanism 34 that is disposed on a cylindrical body 31 that projects at an angle from the tubular body 30. A threaded rod 35 extends through the cylindrical body 31 (see FIG. 5) while a carriage 36 with an upper stabilizing portion/sleeve 44 is threadedly positioned on the threaded shaft 35. Rotation of the sleeve 44 though engagement of a tool (not shown) with the nut 45 disposed at the top of the sleeve 44, moves the carriage 36 up and down on the threaded rod 35.

The carriage 36 of the tensioning sub-assembly 34 carries a laminar fixation tape locking, clamping or retention mechanism to hold the laminar fixation tape for tensioning thereof. Once the laminar fixation tape is locked by and into the tensioning sub-assembly 34, the carriage 36 may be moved as desired to provide a desired tensioning. The carriage 36 includes a radial flange 37 having a clamping arm 38 pivotally connected thereto by pivot 40. An inside surface of the clamping arm 38 has teeth or the like 41. When the clamping arm 38 is in the position shown in FIG. 2, the clamping mechanism is in a tape unlocked state or position which allows the laminar fixation tape to freely move therethrough. When the clamping arm 38 is in the position shown in FIG. 4, the clamping mechanism is in a tape locked state or position which prevents free movement of the laminar fixation tape. The clamping arm 38 also has a generally U-shaped base 39 (see FIG. 8) and defines a first stabilizer 39a, and a second stabilizer 39b that surrounds the cylindrical body 31. An annular shelf 43 of the carriage 36 provides a seat for the first and second stabilizers 39a, 39b.

A method of installation includes threading laminar tape through the laminar fixation implant 11, clamping the laminar fixation implant onto a spine rod, threading the laminar fixation tape into the implant, looping the laminar tape around a lamina, sub-lamina or other vertebral bone/bone portion, then tightening the laminar tape accordingly.

It should be appreciated that dimensions of the components, structures, and/or features of the present laminar fixation implant and installation instrument may be altered as desired within the scope of the present disclosure.

What is claimed is:

1. A laminar fixation system for retaining a spine rod relative to a vertebra of the spine, the laminar fixation system comprising:

a laminar fixation implant defining a top, a bottom, a first lateral side, a second lateral side, a first end, and a second end, the first end having a channel forming an upper extension and a lower extension and configured to receive a spine rod, a first locking mechanism disposed in the upper extension and configured to retain the laminar fixation implant onto a spine rod, a passage extending from the second end to the first end and configured to receive laminar fixation tape, a second locking mechanism extending from the top to the passage, the second locking mechanism configured to fix laminar fixation tape relative to the laminar fixation implant; and a laminar fixation implant installation tool comprising:
a body,
a retention mechanism for holding the laminar fixation implant during installation,
an actuator for manipulating the second locking mechanism of the laminar fixation implant,
a sub-assembly for tensioning laminar fixation tape received in the passage of the laminar fixation implant, the sub-assembly comprising:
a threaded rod coupled to the body,
a sleeve threadably coupled to the threaded rod,
a carriage movably relative to the sleeve,
a clamp disposed on the carriage and configured to releasably retain the laminar fixation tape, and
wherein initial rotation of the sleeve in a first direction actuates the clamp to retain the laminar fixation tape, and wherein continued rotation of the sleeve in the first direction increases the tension in the laminar fixation tape.

2. The laminar fixation system of claim 1, wherein the actuator of the laminar fixation installation tool comprises a threaded shaft with a configured end for manipulating the second locking mechanism of the laminar fixation implant.

3. The laminar fixation system of claim 2, wherein the second locking mechanism of the laminar fixation implant comprises a threaded bore extending from the top to the passage, a ball movably disposed in the threaded bore, and a set screw threadedly received in the threaded shaft axially above the movable ball, the configured end of the actuator of the laminar fixation installation tool received in the set screw, whereby rotation of the threaded shaft of the actuator axially advances the set screw in the threaded bore towards and against the ball to axially move the ball against laminar fixation tape disposed in the passage.

4. The laminar fixation system of claim 1, wherein:
the laminar fixation implant has a first external channel on the first lateral side, and a second external channel on the second lateral side; and
the retention mechanism of the laminar fixation installation tool includes a first tang configured to releasably attach to the first external channel of the laminar fixation implant, and a second tang configured to releasably attach to the second external channel of the laminar fixation implant.

5. The laminar fixation system of claim 4, wherein the first and second external channels of the laminar fixation implant channels are J-shaped.

6. The laminar fixation system of claim 1, wherein the first locking mechanism of the laminar fixation implant comprises a threaded hole extending from a top surface of the upper extension to a lower surface of the upper extension, and a set screw disposed in the threaded hole.

7. The laminar fixation system of claim 1, further comprising a shelf coupled to the sleeve and configured for translating movement along the axis of the threaded rod caused by rotation of the sleeve, wherein the clamp comprises a clamping arm having a first portion pivotally coupled to the carriage and a second portion in contact with the shelf.

8. The laminar fixation system of claim 7, wherein the sub-assembly comprises a hex driver, whereby rotation of the hex driver in the first rotational direction moves the carriage along the threaded rod to provide tensioning of the laminar fixation tape.

9. A method of retaining a spine rod relative to a vertebra comprising:
providing a laminar fixation system having:
a laminar fixation implant defining a top, a bottom, a first lateral side, a second lateral side, a first end, and a second end, the first end having a channel forming an upper extension and a lower extension and configured to receive a spine rod, a first locking mechanism disposed in the upper extension and configured to retain the laminar fixation implant onto a spine rod, a passage extending from the second end to the first end and configured to receive laminar fixation tape, a second locking mechanism extending from the top to the passage, the second locking mechanism configured to fix laminar fixation tape relative to the laminar fixation implant; and a laminar fixation implant installation tool comprising:
a body,
a retention mechanism for holding the laminar fixation implant during installation,
an actuator for manipulating the second locking mechanism of the laminar fixation implant,
a sub-assembly for tensioning laminar fixation tape received in the passage of the laminar fixation implant, the sub-assembly comprising:
a threaded rod coupled to the body,
a sleeve threadably coupled to the threaded rod,
a carriage movably relative to the sleeve,
a clamp disposed on the carriage and configured to releasably retain the laminar fixation tape, and
wherein initial rotation of the sleeve in a first direction actuates the clamp to retain the laminar fixation tape, and wherein continued rotation of the sleeve in the first direction increases the tension in the laminar fixation tape;

providing laminar fixation tape;
clamping the laminar fixation implant onto a spine rod using the first locking mechanism of the laminar fixation implant;
threading the laminar fixation tape through the passage of the laminar fixation implant;
threading the laminar fixation tape into the tensioning sub-assembly;
looping the laminar fixation tape around a lamina of a vertebra;
tensioning the laminar fixation tape using the tensioning sub-assembly; and fixing the laminar fixation tape relative to the laminarfixation implant via the second locking mechanism of the laminar fixation implant.

10. The method of claim 9, wherein the actuator of the laminar fixation installation tool comprises a threaded shaft with a configured end for manipulating the second locking mechanism of the laminar fixation implant.

11. The method of claim 10, wherein the second locking mechanism of the laminar fixation implant comprises a threaded bore extending from the top to the passage, a ball movably disposed in the threaded bore, and a set screw threadedly received in the threaded shaft axially above the movable ball, the configured end of the actuator of the laminar fixation installation tool received in the set screw, whereby rotation of the threaded shaft of the actuator axially advances the set screw in the threaded bore towards and against the ball to axially move the ball against laminar fixation tape disposed in the passage.

12. The method of claim 9, wherein:
the laminar fixation implant has a first external channel on the first lateral side, and a second external channel on the second lateral side; and
the retention mechanism of the laminar fixation installation tool includes a first tang configured to releasably attach to the first external channel of the laminar fixation implant, and a second tang configured to releasably attach to the second external channel of the laminar fixation implant.

13. The method of claim 12 wherein the first and second external channels of the laminar fixation implant channels are J-shaped.

14. The method of claim 9, wherein the first locking mechanism of the laminar fixation implant comprises a threaded hole extending from a top surface of the upper extension to a lower surface of the upper extension, and a set screw disposed in the threaded hole.

15. The method of claim 9, wherein the tensioning sub-assembly comprises: a drive mechanism associated with the carriage and configured to move the carriage through manual actuation.

16. The method of claim 15, wherein the drive mechanism of the sub-assembly comprises a hex driver, whereby rotation of the hex driver in the first rotational direction moves the carriage along the threaded rod to provide tensioning of the laminar fixation tape.

* * * * *